United States Patent
Gevins et al.

[11] Patent Number: 5,817,029
[45] Date of Patent: Oct. 6, 1998

[54] SPATIAL MEASUREMENT OF EEG ELECTRODES

[75] Inventors: Alan S. Gevins, San Francisco; Jian Le, San Mateo, both of Calif.

[73] Assignee: Sam Technology, Inc., San Francisco, Calif.

[21] Appl. No.: 883,022

[22] Filed: Jun. 26, 1997

[51] Int. Cl.$^6$ .................................................... A61B 5/04
[52] U.S. Cl. ............................................................ 600/544
[58] Field of Search ................................... 600/544, 545, 600/383, 595

[56] References Cited

U.S. PATENT DOCUMENTS

| | | | |
|---|---|---|---|
| 4,736,751 | 4/1988 | Gevins et al. | 600/545 |
| 5,038,782 | 8/1991 | Gevins et al. | 600/383 |
| 5,119,816 | 6/1992 | Gevins | 600/383 |
| 5,291,888 | 3/1994 | Tucker | 600/383 |
| 5,331,970 | 7/1994 | Gevins et al. | 600/544 |
| 5,361,773 | 11/1994 | Ives | 600/544 |
| 5,479,934 | 1/1996 | Imran | 600/544 |
| 5,568,816 | 10/1996 | Gevins et al. | 600/544 |

OTHER PUBLICATIONS

Sharbrough et al, "Guidelines for Standard Electrode Position Nomenclature", Am. EEG Soc., 1990.

*Primary Examiner*—Max Hindenburg
*Assistant Examiner*—Charles Marmor, II
*Attorney, Agent, or Firm*—Eliot S. Gerber

[57] ABSTRACT

A method which is accurate and yet relatively simple, rapid and inexpensive for estimating 3-D coordinates of EEG (electroencephalograph) electrode positions on the head. The electrode positions of any number of scalp electrodes placed according to the standard 10/10 electrode position system are computed by a computer system based on 14 manually measured inter-electrode distances and 9 electrode-to-skull landmark straight-line distances. The measurements are made manually using digital calipers.

21 Claims, 4 Drawing Sheets

SPATIAL MEASUREMENT OF EEG ELECTRODES

BACKGROUND OF THE INVENTION

1. Field of the Invention

The present invention relates to EEG (electroencephalograph) instruments used in medicine and science and more particularly to measuring the locations of EEG electrodes on the head of a subject.

2. Related Art

The brain waves of a human subject, at the microvolt level, may be amplified and analyzed using electroencephalograph (EEG) equipment. Generally 19 electrodes are electrically connected to the scalp of the subject and the brain waves are amplified and displayed in analog form. U.S. Pat. No. 4,736,751, incorporated by reference, describes a system using a larger number of electrodes and various digital computer based methods to obtain more information from the brain wave signals.

However, when many electrodes are used, for example, 32–256 electrodes, it is time consuming to obtain their location on the subject's scalp using the conventional techniques of tape measurements or magnetic field position digitization. If the subject is a child, senile or infirm, the subject may not be able to hold still for the 15–45 minutes which may be required for such measurements. The physical location of the electrodes is required to compare the EEG recordings, at each electrode, with the information obtainable concerning the head of the subject from other medical imaging systems, such as MRI (Magnetic Resonance Imaging). Such registration of EEG data with MRI data provides insight about the relationship between neurophysiological function and brain anatomy.

Accurate information about the physical 3-D (three-dimensional) position of each electrode on a subject's head is necessary to take advantage of spatial enhancement techniques, and for accurate registration of EEG data with anatomical images from MRI or CT scans. The means by which the 3-D coordinates of electrode positions are determined is an important practical issue with respect to accuracy, procedure time, cost and flexibility. If it takes too long, or costs too much, to obtain the data, often the experiment or diagnoses may not be conducted.

In terms of accuracy, a method for estimating EEG electrode positions should be accurate enough to designate a point within the effective recording area of an electrode, approximately 1 cm radial for recordings made with a standard electrode cap.

In U.S. Pat. No. 5,119,816, incorporated by reference, a flexible hat is placed on the subject's head and piezoelectric ribbons, embedded in the hat, are stretched. The extent the ribbons are stretched (tensioned) determines the size of the subject's head in the direction along which the ribbon lies. The head measurements are entered into a pattern recognition computer system and the subject's head shape is classified as falling into a class of head shapes. The electrode locations are mathematically derived in a computer system based on the known locations of the corresponding electrodes on a head model in the same head shape class and the size of the subject's head.

An alternative is to measure the position of each electrode on the subject's head using a probe which transmits its 3-D position and touching each electrode with the probe. Various types of probes are a magnetic digitizer or a sonic digitizer, a suitable and commercially available magnetic digitizer being a magnetic field transmitter and receiver (probe) from Polhemus, Colchester, Vermont. However, that type of magnetic digitizer is relatively expensive and may be slow, particularly when many electrodes are recorded. It is easily influenced by stray magnetic fields and so is not reliable in certain hospital and field locations.

Another method which has been suggested, but which is not commercially available, involves using digital cameras and automated image recognition techniques. A method described by De Munck et al, "A practical method for determining electrode positions on the head", *Electroenceph. clin. Neurophysiol.*, 89, 85–87 (1991) requires only a simple tool, such as a pair of compasses or calipers, to measure the distances between each electrode and three fiducial markers. The Cartesian coordinates of each electrode are then computed from the three measurements. Although this direct measurement technique provides precise positional information and does not require specialized equipment, the need to measure three distances per electrode makes the technique too time-consuming to be of practical use in high-resolution EEG studies.

SUMMARY OF THE INVENTION

In accordance with the present invention a new method is provided to measure the physical locations of a large number (32–264) of EEG electrodes which are removably positioned on the scalp of a patient. Using a fabric cap containing 64 electrodes this method has located electrodes with an average (mean) error of 0.3 cm and a maximum mean error of 0.83 cm.

The method is fast and all 64 electrodes have been located in less than 6 minutes. That is sufficiently fast so that the EEG cap may be used even with children and infirm persons.

The method is low in cost as it uses commercially available digital calipers. It is not subject to adverse effects from stray magnetic fields and is simple enough so that it may be implemented by relatively inexperienced personnel.

The present method computes the 3-D positions of any number of standard "10/10" position system scalp electrodes from a set of 14 manually measured straight-line interelectrode distances. This technique is possible because the 10/10 electrode position system is laid out according to a regular pattern, see Sharbrough et al, "Guidelines For Standard Electrode Position Nomenclature", *Am. EEG Soc.* (1990), incorporated by reference.

The measurements are made using a digital caliper.

The 14 measurements are then entered into a computer system. The computer system, using a software program, then calculates the position estimates for the entire set of electrodes, for example, the 64 3-D locations of a set of 64 EEG electrodes on a fabric hat.

DETAILED DESCRIPTION

Figure 1:
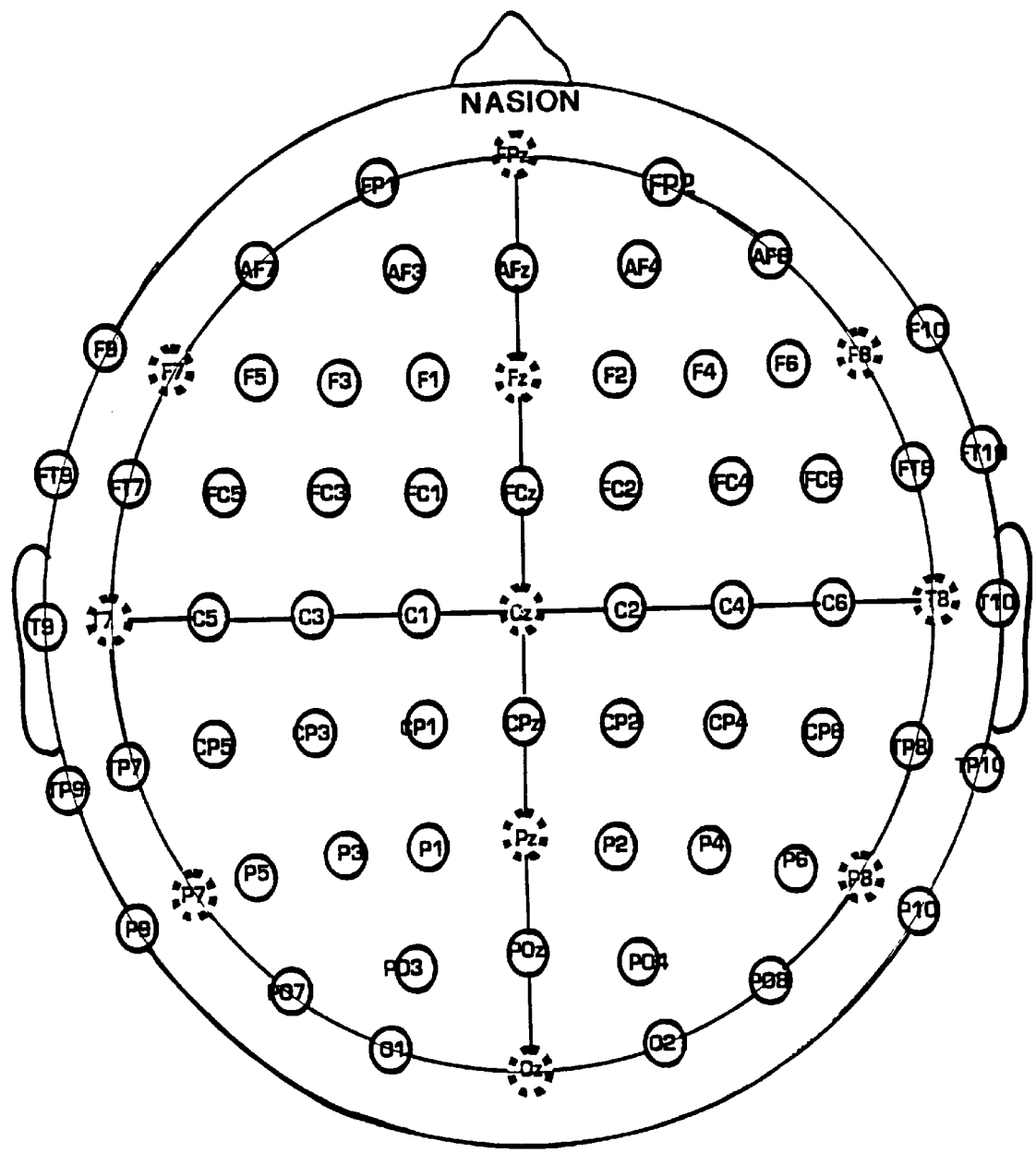
FIG. 1 is a top plan view of the electrodes, and their nomenclature, in the 10/10 EEG placement system.
Figure 2:
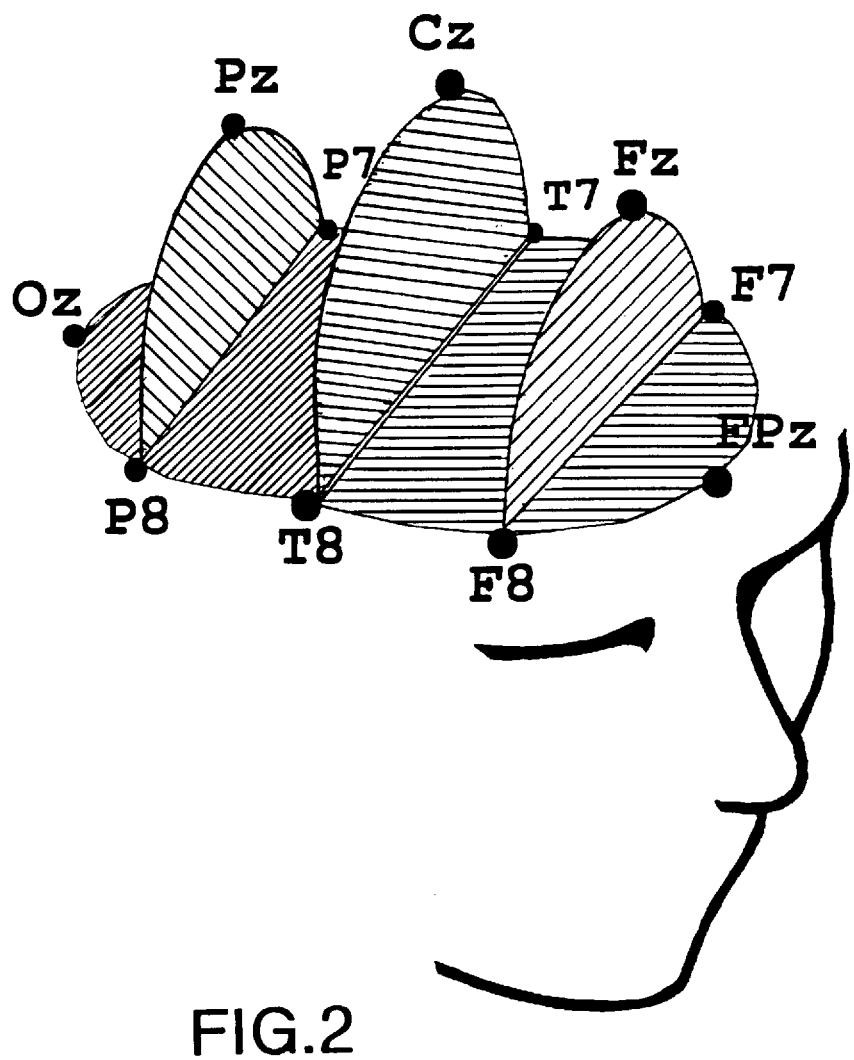
FIG. 2 shows the construction of the five imaginary planes and the measurements of distances between them.

The shape of a person's head can be closely approximated by five planes, each of which is determined by at least three electrodes of the 10/10 position system as follows: 1) F7-Fz-F8, 2) T7-F7-Fpz-F8-T8, 3) T7-Cz-T8, 4) T7-P7-Oz-P8-T8) and 5) P7-Pz-P8, see FIG. 1. The arcs of these five planes along the head's surface are then fitted by perturbed ellipsoids, the shapes of which are constructed by a computer system from direct measurements. Preferably, eight inter-electrode distances are measured to determine the dimensions of three coronal planes (F7-Fz-F8, T7-Cz-T8, P7-Pz-P8) and two horizontal planes (T7-F7-Fpz-F8-T8, T7-P7-Oz-P8-T8). An additional six inter-electrode measurements are used to determine the spatial relationships (the distances) between these planes, see FIG. 2.

Figure 3:
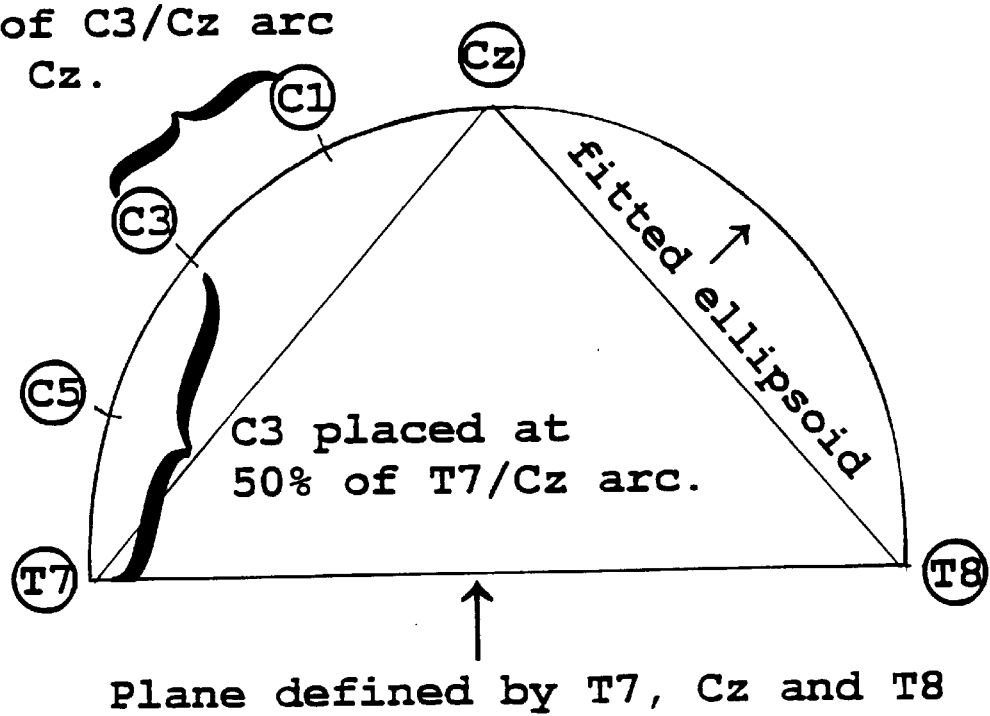
FIG. 3 shows an ellipsoidal curve, the locations of electrodes T7, Cz and T8, and electrodes C1, C3 and C5 located at predetermined spaced distances between them.

These 14 measurements are entered into a computer system which generates perturbed ellipsoidal curves from these distances, passing through eleven electrodes at Fpz, F7, Fz, F8, T7, Cz, T8, P7, Pz, P8, and Oz. Finally, any number of standard 10/10 electrode positions can be calculated by appropriately subdividing the ellipsoidal curves and extrapolating, see FIG. 3. The advantage of this method is that regardless of the number of the electrodes, i.e., 32–264, in the recording montage, only 14 measurements are required to generate the positional information for the entire montage The disadvantage is that it only works for electrodes placed according to the 10/10 system.

The results of a validation study of this technique are reported below. The 3-D coordinates of 64 scalp electrodes placed according to the standard 10/10 system were derived using the technique of the present invention. For comparison, the 3-D coordinates were also measured using a commercial magnetic position measurement system. To determine the relative accuracy of these two techniques, the results of both the positional information obtained from these two techniques were compared to the direct measurement technique of De Munck et al (1991), which was taken as being the most accurate set of measurements.

Methods

Eleven healthy adult subjects (6 male, 5 female) ranging in age from 18 to 36 years were tested. A fabric cap containing 64 electrodes was placed on each subject so that the electrodes were in standard 10/10 positions, (Blum & Annveldt, An electrode cap tested, *Electroenceph. clin. Neurophysiol.*, 54, 591–594, 1982).

Electrode position information was obtained using each of the three following techniques:

1) Direct Measurement: Following the procedure described by De Munck et al (1991) the position of each electrode was measured with respect to each of the three reference landmarks (T7, FPZ and T8) using a pair of 12-inch digital calipers (Mitutoyo, Inc.). A total of 192 measurements were made. The 3-D Cartesian coordinates for each electrode were then derived as described by De Munck et al (1991).

2) Magnetic Digitization: The 3-D coordinates of the 64 electrode positions, in addition to the nasion, left and right preauricular notches, were obtained using a position digitizer which has a magnetic field transmitter and receiver (Polhemus, Colchester, Vermont). The subject's head was fixed in a stationary position using a head holder which contained the magnetic field source. Each electrode and skull landmark was touched with the tip of the transmitter's wand (probe) and the position entered into the computer.

3) Method Of The Present Invention: Fourteen inter-electrode distances were measured using the same 12-inch digital calipers employed in technique 1. The following is a list of the 14 measured distances:

| | |
|---|---|
| T7 to T8, | P7 to P8, |
| T7 to Cz, | P7 to Pz, |
| T7 to Fpz, | P7 to Oz, |
| T7 to Oz, | Fpz to Fz, |
| F7 to F8, | Fz to Cz, |
| F7 to Fz, | Cz to Pz, |
| F7 to Fpz, | Pz to Oz |

To determine the relative position of the electrode montage to the fiducial landmarks (points on the head), an additional nine measurements were performed. The distance between each fiducial point (nasion, left and right preauricular notches) and electrodes T7, T8 and Fpz was measured.

Placement of the recording cap as well as measurements of the electrode positions were carried out by the same experienced technician. A stopwatch was used to measure the elapsed time (rounded to the nearest 15 seconds) for each of the three methods.

The 3-D Cartesian coordinates of each electrode obtained using the technique of the present invention and the magnetic digitizer were compared with the results obtained using the direct measurement technique. Table 1 illustrates that the error, defined as the average distance between each of the 64 electrode positions determined by the two test methods and the direct measurement technique, is significantly smaller for the invention method (0.3 cm) than for the magnetic field digitization method (0.36 cm) (paired t-test $t(10)=-2.91$, $p <0.02$). The difference in the mean standard deviation of the error between the invention method and magnetic digitization suggests that the computational method is less variable (0.03 cm vs. 0.05 cm respectively).

The time required to measure the coordinates of each electrode position (64 electrodes) using the direct measurement technique was exceedingly long, usually taking over 1 hour. In contrast, the inventive method took an average of 5.66 minutes, and magnetic digitization took an average of 7.95 minutes (table 1). The inventive method was significantly faster than the magnetic field digitization method (paired t-test, $t(10)=-7.98$, $p <0.001$).

Discussion

Both the inventive method and the magnetic field digitization method are sufficiently accurate to determine an electrode location within the 0.7 cm inner diameter of a typical electrode casing, for example, the casings used in an ECI (Electro-Cap International) electrode cap. This is also well below the average effective electrode contact area of approximately 3 cm$^2$ due to average electrode gel spread of approximately 1 cm radial. The advantage of the inventive method over the magnetic field digitization method is that it is faster, uses readily available inexpensive equipment and is not subject to magnetic fields. A limitation of the inventive method is that it requires that electrodes be applied according to the standard 10/10 system of electrode placement, whereas the magnetic field digitizer can provide coordinates for any position on the head. However, a hybrid system of direct manual measurements (as in the direction measurement method of De Munck) and the computational method of the inventive method can be utilized for montages with a few non-standard electrode positions, as was done to determine the positions of skull landmarks in this example. Another disadvantage is that if electrodes are not actually placed at the correct intended 10/10 electrode position, the computed electrode position will be erroneous. Considering that the effective size of an electrode's contact area with the scalp is determined by the size of the electrode gel patch, which is of the order of 1 cm, radial, and that the center-to-center distance between electrodes on an adult head with 128 electrodes is of the order of 2.5 cm, the deviation of the actual electrode placement from the intended 10/10 electrode position would have to be of the order of 0.5 cm or more, and therefore obvious to the technician, to be of practical concern.

The efficiency advantage of the inventive method increases as the number of electrodes increases, since the same 14 measurements are required regardless of the number of electrodes in the recording montage. In contrast, the amount of time required to operate the magnetic digitizer is directly related to the number of electrode positions which have to be measured. Thus, for 128 electrodes, the inventive method would still take less than 6 minutes, while the magnetic field digitization method would require more than 15 minutes. With regard to cost, a commercial magnetic digitizer costs about five times as much as a pair of good quality 12-inch digital calipers. Additionally, the calipers are very compact and rugged, require no external power, and can be used in any setting. The magnetic field digitization device is more delicate, uses electrical power, requires either a device to hold the head in place or a device to position an extra receiver on the head, and cannot be used close to large metallic objects, such as hospital beds or filing cabinets. These factors have practical relevance when high resolution EEG records are made outside the laboratory environment, i.e., on a hospital ward or in the field.

TABLE 1

Procedure time and electrode position accuracy for the inventive method and the magnetic field position digitizing method for determining the positions of 64 electrodes plus three skull landmarks in each of 11 subjects. Error is defined as the average distance between the positions determined with the new or magnetic field digitization methods and the direct measurement method (De Munck et al 1991) for all 64 electrodes. "Max." is the maximum electrode position error.

|  | New Method | Magnetic Field Device | New Method Error (cm) | | Magnetic Field Device Error (cm) | |
|---|---|---|---|---|---|---|
|  | Procedure time | (minutes) | avg | max | avg | max |
| Subject |  |  |  |  |  |  |
| 1 | 7.00 | 8.50 | 0.30 | 0.72 | 0.28 | 0.93 |
| 2 | 6.50 | 8.00 | 0.29 | 0.83 | 0.46 | 1.31 |
| 3 | 6.00 | 8.00 | 0.32 | 0.87 | 0.40 | 1.14 |
| 4 | 5.75 | 9.00 | 0.33 | 0.94 | 0.34 | 1.11 |
| 5 | 5.00 | 8.50 | 0.29 | 0.92 | 0.33 | 0.72 |
| 6 | 6.00 | 7.50 | 0.23 | 0.58 | 0.33 | 0.82 |
| 7 | 5.00 | 8.00 | 0.27 | 0.85 | 0.40 | 1.11 |
| 8 | 5.00 | 9.00 | 0.34 | 0.91 | 0.36 | 0.89 |
| 9 | 5.50 | 7.50 | 0.33 | 0.78 | 0.35 | 0.82 |
| 10 | 5.50 | 7.00 | 0.34 | 1.08 | 0.33 | 1.11 |
| 11 | 5.00 | 6.50 | 0.31 | 0.67 | 0.35 | 1.34 |
| mean | 5.66 | 7.95 | 0.30 | 0.83 | 0.36 | 1.03 |
| std dev. | 0.67 | 0.79 | 0.03 | 0.14 | 0.05 | 0.20 |

Figure 4:
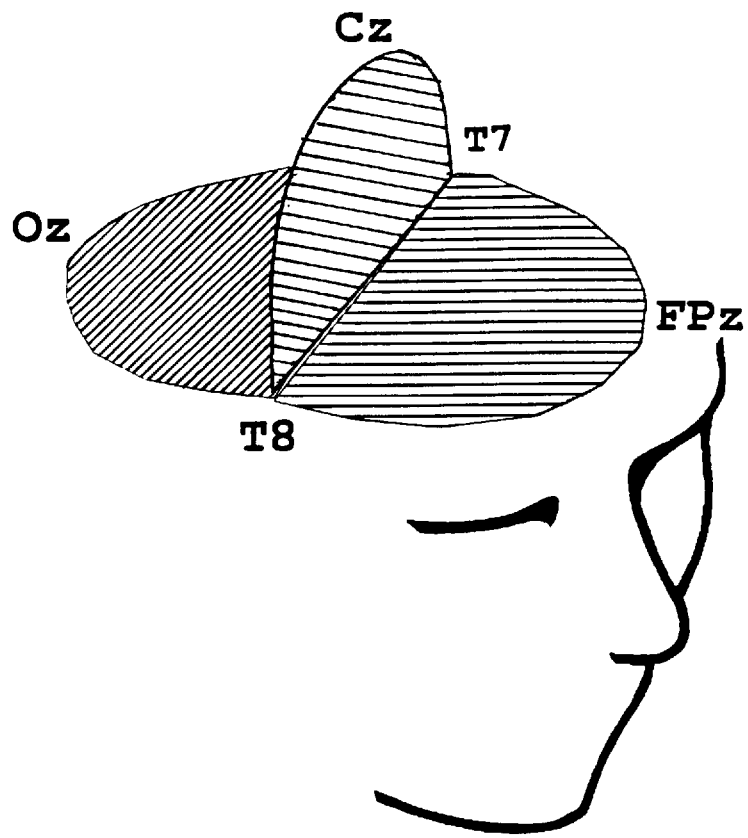
FIG. 4 shows the construction of three imaginary planes.

Alternatively, the method of the present invention may be implemented using fewer measurements. It is believed that six is the minimum number of electrode position measurements that are required. FIG. 4 shows only one coronal plane (T8, CZ, T7) and two horizontal planes (T8, FPZ, T7) and (T8, OZ, T7). In the embodiment of FIG. 4 the positions of only five electrodes are measured along with at least one fiducial measurement.

As in the prior embodiment (FIG. 2) the positions of the measured electrodes and fiducial points are entered into a computer and the estimated positions of all the electrodes are then derived, as in the prior embodiment.

What is claimed is:

1. A method of locating the 3-D (3-dimensional) positions of a set of 32 or more EEG (electroencephalograph) electrodes removably positioned on the head of a subject comprising:
   (a) placing the electrodes on the head with eleven of the electrodes positioned in a 10/10 placement;
   (b) placing the other electrodes on the head in predetermined spaced relationship between the eleven electrodes of (a);
   (c) measuring the distances between the eleven electrodes of (a);
   (d) entering the measured distances of (c) into a computer system and based thereon computing estimates of the 3-D positions of the other electrodes of the set of electrodes.

2. A method as in claim 1 wherein the set consists of 64 EEG electrodes.

3. A method as in claim 1 wherein the other electrodes of (b) are placed at equal distances from the eleven electrodes or from each other.

4. A method as in claim 1 wherein the measurements are made by operation of digital calipers.

5. A method as in claim 1 wherein the computation of (d) is based upon imaginary curves formed in a plurality of planes.

6. A method as in claim 5 wherein the curves are ellipsoids.

7. A method as in claim 5 wherein at least three of the planes are spaced apart.

8. A method as in claim 1 wherein in (c) eight inter-electrode distances are measured to determine three coronal planes and two horizontal planes, and six inter-electrode distances are measured to determine the distances between the five planes.

9. A method as in claim 8 and, in the computer system, generating perturbed ellipsoidal curves from the 14 inter-electrode distances and computing the estimates of the 3-D positions of the other electrodes by subdividing the ellipsoidal curves and extrapolating.

10. A method as in claim 8 and also performing a plurality of position measurements to determine a plurality of fiducial landmarks on the subject's head and distances from the fiducial landmarks to at least some of the eleven electrodes.

11. A method as in claim 10 wherein the fiducial landmarks comprise the nasion, left and right preauricular notches.

12. A method as in claim 11 wherein the set of electrodes are positioned in a stretch cap on the subject's head.

13. A method of locating the 3-D (3-dimensional) positions of a set of 32 or more EEG (electroencephalograph) electrodes removably positioned on the head of a subject comprising:
   (a) placing the electrodes on the head with at least five of the electrodes positioned in a 10/10 placement;
   (b) placing the other electrodes on the head in a predetermined spaced relationship between the five electrodes of (a);
   (c) measuring the distances between the five electrodes of (a);
   (d) entering the measured distances of (c) into a computer system and based thereon computing estimates of the 3-D positions of the other electrodes of the set of electrodes.

14. A method as in claim 13 wherein the set consists of 64 EEG electrodes.

15. A method as in claim 13 wherein the other electrodes of (b) are placed at equal distances from the five electrodes or from each other.

16. A method as in claim 13 wherein the measurements are made by operation of digital calipers.

17. A method as in claim 16 wherein the curves are ellipsoids.

18. A method as in claim 17 and, in the computer system, generating ellipsoidal curves from the measured inter-electrode distances and computing the estimates of the 3-D positions of the other electrodes by subdividing the ellipsoidal curves and extrapolating.

19. A method as in claim 13 and also performing a plurality of position measurements to determine a plurality of fiducial landmarks on the subject's head and distances from the fiducial landmarks to at least some of the five electrodes.

20. A method as in claim 13 wherein the fiducial landmarks comprise the nasion, left and right preauricular notches.

21. A method as in claim 13 wherein the set of electrodes are positioned in a stretch cap on the subject's head.

* * * * *